US00PP30967P2

(12) United States Plant Patent
Van Dijk

(10) Patent No.: US PP30,967 P2
(45) Date of Patent: Oct. 22, 2019

(54) ***ANTHURIUM* PLANT NAMED 'ANTHGLYNT'**

(50) Latin Name: ***Anthurium andraeanum* L.**
Varietal Denomination: ANTHGLYNT

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,440

(22) Filed: Nov. 16, 2018

(51) Int. Cl.
*A01H 5/02* (2018.01)
*A01H 6/00* (2018.01)

(52) U.S. Cl.
USPC ..... Plt./369

(58) Field of Classification Search
USPC ..... Plt./369
CPC ..... A01H 5/002; A01H 6/00
See application file for complete search history.

*Primary Examiner* — Annette H Para
(74) *Attorney, Agent, or Firm* — Jondle & Associates, P.C.

(57) ABSTRACT

A new *Anthurium* plant named 'ANTHGLYNT' particularly distinguished by having very shiny and blistered, bright red, cordate and very durable spathes that retain the original color for a very long period of time, spathes positioned high above the foliage, white spadices with yellow-green tips, deltoid and durable leaves, early and rich flowering continuously throughout the year, and a plant height of 21.0 cm to 26.0 cm is disclosed.

3 Drawing Sheets

Genus and species: *Anthurium andraeanum* L.
Variety denomination: 'ANTHGLYNT'.

BACKGROUND OF THE NEW PLANT

The present invention comprises a new and distinct variety of *Anthurium*, botanically known as *Anthurium andraeanum* L., and hereinafter referred to by the variety name 'ANTHGLYNT'. The new *Anthurium* plant is a product of a planned breeding program conducted by the inventor in Bleiswijk, the Netherlands. The objective of this breeding program was to create a new 21.0 cm to 26.0 cm height plant with very shiny and blistered, bright red, cordate and very durable spathes.

The new variety originated from a cross-pollination made in February 2011 in Bleiswijk, The Netherlands. The female parent was a red *Anthurium* pot plant designated '11125-01' (unpatented), and the male parent was a red *Anthurium* plant designated '16154-01' (unpatented).

A single plant was selected from the progeny of the stated cross in November 2012. Asexual reproduction of the new variety by tissue culture in 2015 in Bleiswijk, The Netherlands, has demonstrated that the new variety reproduces true to type with all of the characteristics, as herein described, firmly fixed and retained through successive generations.

Plant Breeder's Rights for this variety have been applied for in the European Union on Nov. 27, 2017. 'ANTHGLYNT' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Very shiny and blistered, bright red, cordate spathes;
2) White spadices with yellow-green tips;
3) Green, deltoid leaves; and
4) Spathes positioned high above the foliage.

DESCRIPTION OF THE PHOTOGRAPHS

This new *Anthurium* plant is illustrated by the accompanying photographs which show the overall plant habit including blooms, bud and foliage of the plant; the colors shown are as true as can be reasonably obtained by conventional photographic procedures. The photographs are of a 28-week old plant grown in a greenhouse in Bleiswijk, The Netherlands, in October 2018. Colors in the photographs may differ from the color values cited in the detailed botanical description, which accurately describe the actual colors of the new variety.

DESCRIPTION OF THE NEW VARIETY

Figure 1:
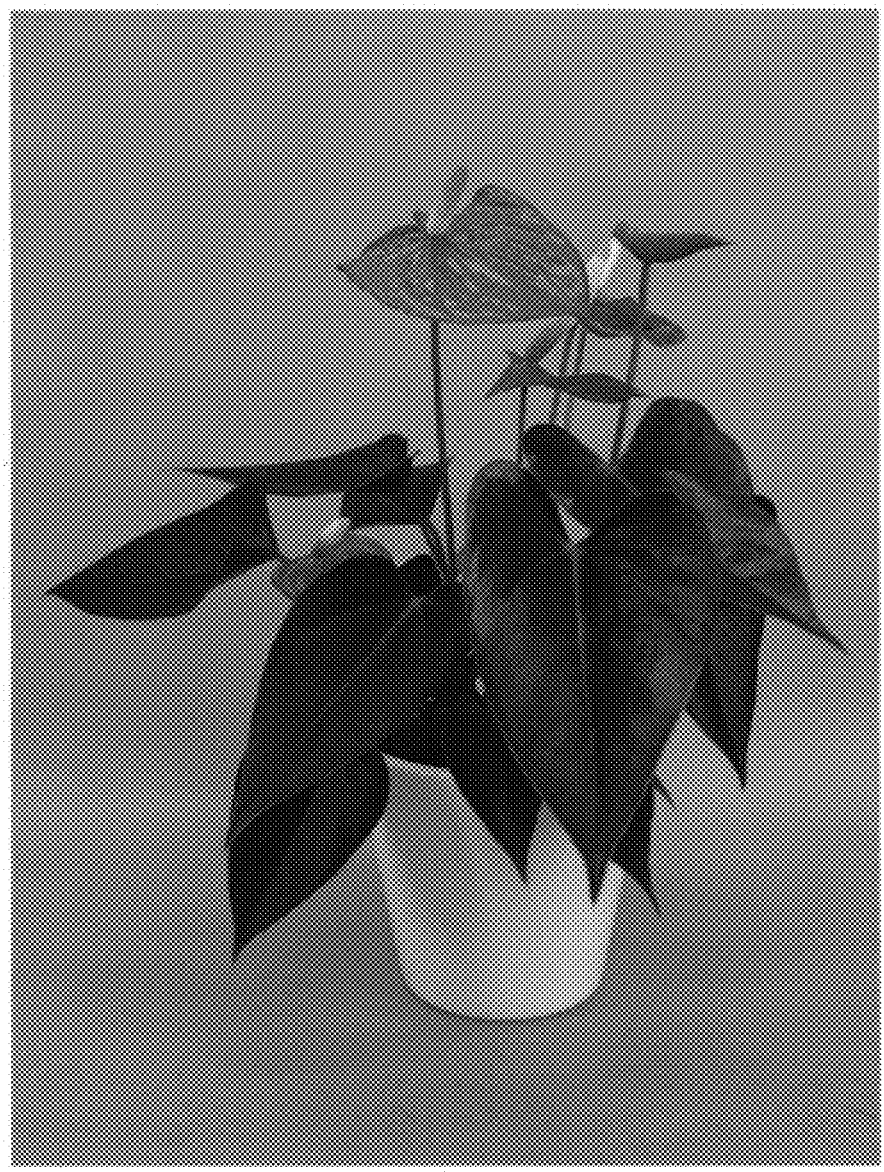
FIG. 1 shows the overall plant habit, including blooms, bud and foliage.
Figure 2:
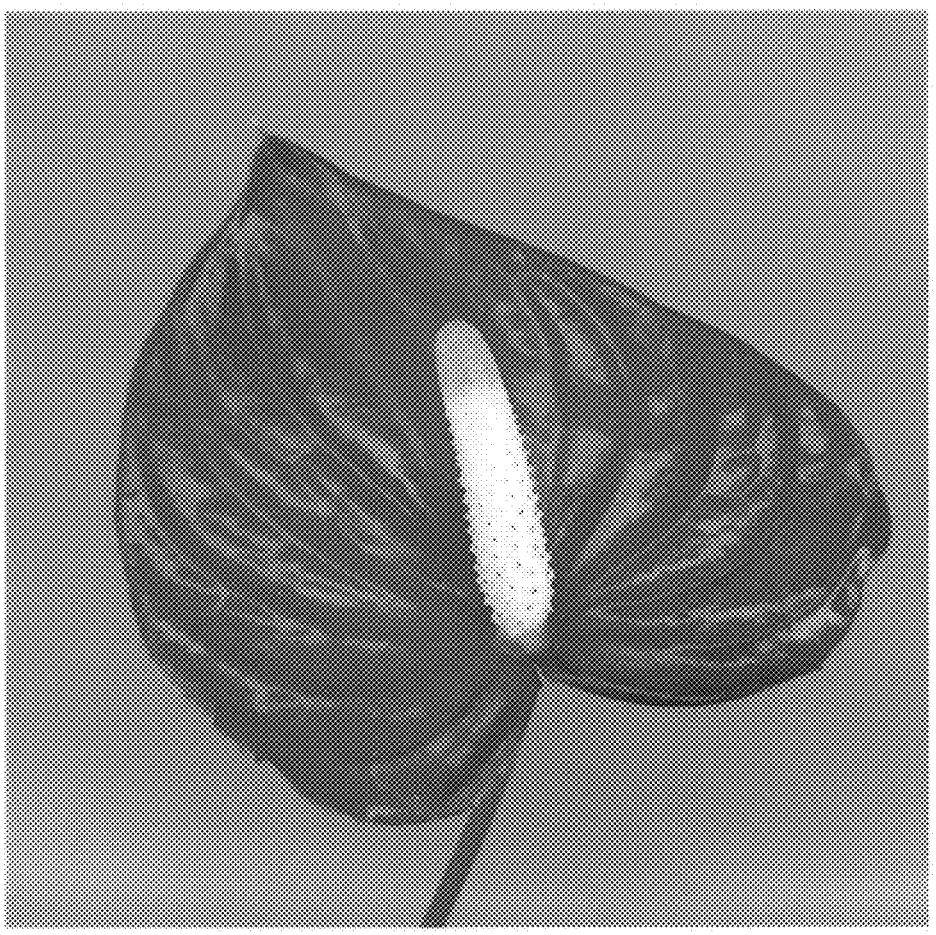
FIG. 2 shows a close-up of the mature spathe.
Figure 3:
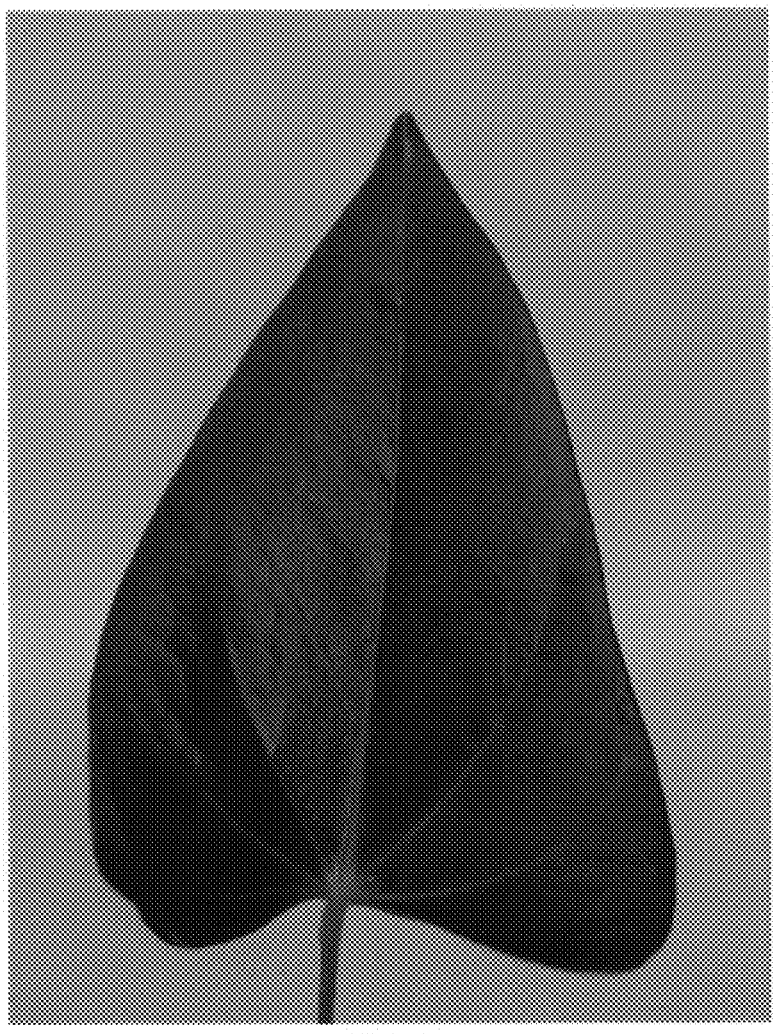
FIG. 3 shows a close-up of the upper leaf blade surface.

The following detailed description sets forth the distinctive characteristics of 'ANTHGLYNT'. The data which define these characteristics were collected from asexual reproductions carried out in Bleiswijk, The Netherlands. The plant history was taken on 28-week old plants which were planted from tissue culture in 9 centimeter (diameter) pots and grown in a glass greenhouse between 19° C. and 24° C. Observations were made in October 2018. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHGLYNT'.

Parentage:

*Female parent*.—*Anthurium* plant '11125-01' (unpatented).

*Male parent*.—*Anthurium* plant '16154-01' (unpatented).

Plant:

*Propagation*.—Tissue culture.

*Root description*.—Fleshy, light greenish-yellow colored roots with small hairy lateral roots having yellow colored root tips.

*Time to produce a finished flowering plant*.—26 to 30 weeks after planting in a 9 cm (diameter) pot.

*Growth habit*.—Upright.

*Height* (*measured from soil, including inflorescence*) .—21.0 cm to 26.0 cm.

*Width* (*measured from leaf tips*).—29.0 cm to 33.0 cm.

Leaves:

*Immature leaves*.—Length: 10.0 cm to 12.0 cm. Width: 7.0 cm to 8.0 cm. Color: Upper surface: RHS 146A. Lower surface: RHS 146B. Texture (both upper and lower surfaces): Shiny, soft and smooth.

*Mature leaves*.—Length (fully expanded): 12.0 cm to 14.0 cm. Width: 8.0 cm to 9.0 cm. Shape: Deltoid. Apex: Acuminate. Base: Cordate. Leaf blade angle with the petiole: Between 90 degrees and 110 degrees. Leaf margin: Entire. Color: Upper surface: RHS 147A. Lower surface: RHS 146A. Texture (both upper and lower surfaces): Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Present. Arrangement: Leaf blade has two lobes extending past the petiole. The lobes are non-touching. Length of lobes of mature leaf blades: 0.5 cm to 1.5 cm. Width of lobes of mature leaf blades: 3.0 cm to 4.0 cm. Distance from petiole/leaf junction to highest point on lobes of mature leaf: 2.0 cm to 3.0 cm.

*Petiole*.—Cross-section: Round. Diameter: 0.2 cm to 0.3 cm. Length: 10.0 cm to 12.0 cm for a mature leaf size. Color: Mature leaf: RHS 144A. Immature leaf: RHS 144B. Cataphyll color surrounding the petiole: Outside: RHS 144C. Inside: RHS 144D.

*Geniculum*.—Length: 1.0 cm to 1.5 cm. Width: 0.3 cm to 0.4 cm. Color: RHS 144A.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 80 degrees and 100 degrees; the spathe stands on a wiry peduncle about 6.0 cm to 9.0 cm above the foliage.

*Shape*.—Cordate.

*Apex*.—Caudate.

*Base*.—Cordate.

*Texture*.—Very shiny and blisterer.

*Margin*.—Undulated.

*Size*.—Length: 7.5 cm to 8.5 cm. Width: 6.5 cm to 7.5 cm.

*Lobes*.—Present.

*Arrangement*.—The spathe has two lobes extending past the peduncle. The lobes are non-touching. Length: 1.5 cm to 2.0 cm. Width: 2.5 cm to 3.5 cm.

*Color*.—Just fully open: Upper surface: RHS 45B. Lower surface: RHS 45C. This bright red color remains for a very long period, at least more than 30 weeks after opening.

Peduncle:

*Shape*.—Erect.

*Cross-section*.—Round.

*Length*.—17.0 cm to 22.0 cm.

*Diameter*.—0.2 cm to 0.3 cm.

*Color*.—RHS 144B.

Flowering time:

*General*.—One small, rooted, untreated tissue culture plant of 8.0 cm tall will flower, depending on the season, after 26 to 30 weeks and 5 to 6 blossoms appear. More blossoms appear after some additional weeks so that a full flowering and commercial plant will have 6 to 7 bright red spathes. Smaller blossoms may occur on immature plants.

Spadix:

*Size*.—Length: 2.0 cm to 3.0 cm (depending on flower size). Width (at apex): 0.5 cm to 0.6 cm. Width (at base): 0.6 cm to 0.7 cm.

*Shape*.—Columnar.

*Angle from spadix tip to peduncle*.—130 degrees to 160 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 15A and 151B. Mature: RHS NN155A. Ages to: RHS 144A.

Flowers:

*Quantity per spadix*.—80 to 120.

*Spadix flower arrangement*.—Bisexual, rounded in cross-section.

*Shape*.—Rounded.

*Size*.—Length: 0.05 cm to 0.10 cm. Diameter (maximum): 0.10 cm. Color: RHS 156D.

Reproductive organs:

*Stamens*.—Not visible.

*Pollen amount*.—Absent.

*Pistil*.—Quantity: 80 to 120. Length: Less than 0.01 cm. Color: RHS 156D.

*Style*.—Not observed to date.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed to date.

COMPARISON WITH PARENTAL AND SIMILAR COMMERCIAL VARIETIES

'ANTHGLYNT' differs from the female parent plant '11125-01' (unpatented) in that 'ANTHGLYNT' has cordate spathes with caudate apexes and medium blistering, whereas '11125-01' has oblong cordate spathes with mucronate apexes and strong blistering.

'ANTHGLYNT' differs from the male parent plant '16154-01' (unpatented) in that 'ANTHGLYNT' has spathes with caudate apexes and medium blistering, and cataphylls with an outside color of green, whereas '16154-01' has spathes with abruptly acuminated apexes and light blistering, and cataphylls with an outside color that is a mix of red and green.

'ANTHGLYNT' differs from similar commercial variety 'ANTHEOZO' (U.S. Plant Pat. No. 27,916) in that 'ANTHGLYNT' has deltoid leaves and spathes with caudate apexes and undulated margins, whereas 'ANTHEOZO' ovate-cordate leaves and spathes with broad acuminate apexes and entire margins.

'ANTHGLYNT' differs from similar commercial variety 'ANTHDUNDAL' (U.S. Plant Pat. No. 27,287) in that 'ANTHGLYNT' has weak shoot formation and spathes with caudate apexes and undulated margins, whereas 'ANTHDUNDAL' has rich shoot formation and spathes with acuminate apexes and entire margins.

I claim:

1. A new and distinct variety of *Anthurium* plant named 'ANTHGLYNT', substantially as illustrated and described herein.

* * * * *